US010857229B2

(12) United States Patent
Bach et al.

(10) Patent No.: US 10,857,229 B2
(45) Date of Patent: Dec. 8, 2020

(54) TREATMENT OF OVARIAN CANCER IN PATIENTS WITH ASCITES USING A SPECIFIC BINDING AGENT OF HUMAN ANGIOPOIETIN-2 IN COMBINATION WITH A TAXANE

(71) Applicant: AMGEN INC., Thousand Oaks, CA (US)

(72) Inventors: Bruce Allen Bach, Thousand Oaks, CA (US); Florian Vogl, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 278 days.

(21) Appl. No.: 15/570,279

(22) PCT Filed: Apr. 28, 2016

(86) PCT No.: PCT/US2016/029747
§ 371 (c)(1),
(2) Date: Oct. 27, 2017

(87) PCT Pub. No.: WO2016/176427
PCT Pub. Date: Nov. 3, 2016

(65) Prior Publication Data
US 2018/0169231 A1 Jun. 21, 2018

Related U.S. Application Data

(60) Provisional application No. 62/155,330, filed on Apr. 30, 2015.

(51) Int. Cl.
A61K 39/395 (2006.01)
A61K 31/337 (2006.01)
C07K 14/475 (2006.01)
A61K 47/68 (2017.01)
A61P 35/00 (2006.01)
A61K 31/282 (2006.01)
A61K 33/24 (2019.01)
A61K 39/00 (2006.01)
G01N 33/574 (2006.01)

(52) U.S. Cl.
CPC ........ A61K 39/3955 (2013.01); A61K 31/282 (2013.01); A61K 31/337 (2013.01); A61K 33/24 (2013.01); A61K 47/6803 (2017.08); A61P 35/00 (2018.01); C07K 14/475 (2013.01); A61K 2039/545 (2013.01); A61K 2300/00 (2013.01); C07K 2319/30 (2013.01); G01N 33/57449 (2013.01)

(58) Field of Classification Search
CPC .............. A61K 31/337; A61K 2300/00; C07K 14/475; C07K 14/515
See application file for complete search history.

(56) References Cited

U.S. PATENT DOCUMENTS 7,138,370 B2 11/2006 Oliner et al.
8,030,025 B2 10/2011 Boone et al.

FOREIGN PATENT DOCUMENTS

| WO | 00/24782 A2 | 5/2000 |
| WO | 03/057134 A2 | 7/2003 |
| WO | 2006/045049 A1 | 4/2006 |
| WO | 2006/068953 A2 | 6/2006 |
| WO | 2007/124090 A2 | 11/2007 |
| WO | 2011/038139 A1 | 3/2011 |

OTHER PUBLICATIONS

Liontos et al (Onco Targets and Therapy, 2014, vol. 7, pp. 1837-1845) (Year: 2014).*
Monk et al (Gynecologic Oncology, 2016, vol. 143, pp. 27-34) (Year: 2016).*
Karlan et al (Journal of Clinical Oncology, 2012, vol. 30, pp. 362-371) (Year: 2012).*
Bergers and Hanahan (2008), "Modes of resistance to anti-angiogenic therapy", Nature Rev. Cancer, 8(8):592-603.
Ebos et al. (2009), "Tumor and host-mediated pathways of resistance and disease progression in response to antiangiogenic therapy", Clin. Cancer Res., 15(16):5020-5025.
Eskander and Tewari (2012), "Emerging treatment options for management of malignant ascites in patients with ovarian cancer", Int'l. J. Women's Health, 4:395-404.
Gale and Yancopoulos (1999), "Growth factors acting via endothelial cell-specific receptor tyrosine kinases: VEGFs, angiopoietins, and ephrins in vascular development", Genes & Dev., 13:1055-1066.
Kipps et al. (2013), "Meeting the challenge of ascites in ovarian cancer: new avenues for therapy and research", Nature Rev. Cancer, 13(4):273-282.
Marchetti et al. (2015), "Advances in anti-angiogenic agents for ovarian cancer treatment: The role of trebananib (AMG 386)", Critical Rev. Oncol./Hematol., 94(3):302-310.
Monk et al. (2014), "Anti-angiopoietin therapy with trebananib for recurrent ovarian cancer (TRINOVA-1): a randomised, multicentre, double-blind, placebo-controlled phase 3 trial", The Lancet Oncol., 15:799-808.
Oliner et al. (2004), "Suppression of angiogenesis and tumor growth by selective inhibition of angiopoietin-2", Cancer Cell, 6: 507-516.
Silverman et al. (2005), "Multivalent avimer proteins evolved by exon shuffling of a family of human receptor domains", Nature Biotech., 23(12):1556-1561.

(Continued)

Primary Examiner — Karen A. Canella
(74) Attorney, Agent, or Firm — Henry P. Wu

(57) ABSTRACT

Methods and compositions for treating ovarian cancer in a human patient with ascites by administering a therapeutically effective amount of an Ang2 inhibitor in combination with a taxane.

18 Claims, No Drawings
Specification includes a Sequence Listing.

(56) References Cited

OTHER PUBLICATIONS

Wendling, Patrice (Jun. 5, 2015), "ASCO: Ascites may salvage trebananib in recurrent ovarian cancer", Conference coverage from the annual meeting of NAMS, Ob. Gyn. News.
International Search Report for PCT/US2016/029747 dated Aug. 11, 2016.

* cited by examiner

TREATMENT OF OVARIAN CANCER IN PATIENTS WITH ASCITES USING A SPECIFIC BINDING AGENT OF HUMAN ANGIOPOIETIN-2 IN COMBINATION WITH A TAXANE

CROSS-REFERENCE TO RELATED APPLICATIONS

This application is the U.S. National Phase of International Application No. PCT/US2016/029747, filed Apr. 28, 2016 and published in English, which claims the benefit of U.S. Provisional Application No. 62/155,330 filed Apr. 30, 2015, which is incorporated by reference herein.

SEQUENCE LISTING

The instant application contains a Sequence Listing which has been submitted in ASCII format via EFS-Web and is hereby incorporated by reference in its entirety. Said ASCII copy, created on Feb. 22, 2018, is named A-1986-US-PCT ST25.txt and is 7,183 bytes in size.

FIELD OF THE INVENTION

The present invention relates to a method of treating ovarian cancer in a human patient with ascites by administering a therapeutically effective amount of an Ang2 inhibitor in combination with a taxane.

BACKGROUND OF THE INVENTION

Angiogenesis, the formation of new blood vessels from existing ones, is essential to many physiological and pathological processes. Angiogenesis is normally tightly regulated by pro- and anti-angiogenic factors. However, in cancer, ocular neovascular diseases, arthritis, and psoriasis, the process can go awry. Folkman, *J., Nat. Med.,* 1:27-31 (1995).

Although many signal transduction systems have been implicated in the regulation of angiogenesis, one of the best-characterized and most endothelial cell-selective systems involves the Tie2 receptor tyrosine kinase (NCBI Reference No. NP_000450.2; referred to as "Tie2" or "Tie2R" (also referred to as "ORK"); murine Tie2 is also referred to as "tek") and its ligands, the angiopoietins (Gale, N. W. and Yancopoulos, G. D., *Genes Dev.* 13:1055-1066 (1999)). There are 4 known angiopoietins (which are cytokines); angiopoietin-1 ("Ang1") through angiopoietin-4 ("Ang4"). These angiopoietins are also referred to as "Tie2 ligands." Angiopoietin-1 and -2 (Ang1 and Ang2) act as ligands for the endothelial specific receptor Tie2. Ang1 plays a role in maintaining vessel integrity, and this is inhibited by Ang2 allowing loosening of endothelial cells with cellular matrix and vascular remodeling. Hanahan et al., *Cell,* 100: 57-70 (2000); Bergers et al., *Nat. Rev. Cancer,* 8:592-603 (2008); and Augustin et al. *Nat. Rev. Mol. Cell Biol.,* 10:165-177 (2009).

Published studies have purportedly demonstrated Tie2 signaling via Ang2 ligand receptor interaction in disease states associated with angiogenesis. Most of these studies have focused on cancer, in which many tumor types appear to express Ang2. In contrast with its expression in pathological angiogenesis, Ang2 expression in normal tissues is extremely limited (Maisonpierre, P. C., et al., (1997), supra; Mezquita, J., et al., *Biochemical and Biophysical Research Communications,* 260:492-498 (1999)). In the normal adult, the three main sites of angiogenesis are the ovary, placenta, and uterus; these are the primary tissues in normal (i.e., non-cancerous) tissues in which Ang2 mRNA has been detected.

As of 2011, there were an estimated 188,867 women living with ovarian cancer in the United States. An estimated 21,980 new cases of ovarian cancer were diagnosed in 2014, representing 1.3% of all new cancer cases. In addition, ovarian cancer accounted for an estimated 14,270 deaths in 2014, representing 2.4% of all cancer deaths. Surveillance, Epidemiology, and End Results ("SEER") at the National Institutes of Health Stat Fact Sheets (http://seer.cancer.gov/statfacts/html/ovary.html; accessed Mar. 16, 2015).

Ascites, the accumulation of fluid in the abdomen, occurs in a significant amount of patients with cancer, including ovarian cancer. Ascites may contribute or play a role in a variety of symptoms including fatigue; early satiety; compromised respiratory, gastrointestinal, and urinary systems function; and may cause abdominal pain. Tan et al., *Lancet Oncology,* 7(11): 925-934 (2006). Moreover, ovarian cancer is the leading cause of malignant ascites in females. Parsons et al., *Eur. J. Surg. Oncol.,* 22:237-239 (1996); and Hata et al., *Gynecol. Oncol.,* 93:215-222 (2004). Epithelial ovarian cancer most frequently disseminates through the transcoelomic route (i.e., penetrating the surface of the peritoneal surface). One of the accepted explanations for tumor cell detachment from the primary tumor and its migration via the coelom is the fluid medium provided by the ascitic fluid. For example, ascitic fluid contains cytokines which facilitate the epithelial-mesenchymal transition (EMT) thought to be important in dissemination of the disease throughout the peritoneal cavity. In addition, transcoelomic metastases contribute substantially to the morbidity associated with ovarian cancer. Tan et al., *Lancet Oncology,* 7(11): 925-934 (2006).

Although ascites in newly diagnosed ovarian cancer patients may be treated with standard treatment methods for the underlying cancer (i.e., i.v. platinum and taxol-based chemotherapy), large volumes of ascites are problematic once drug resistance and cancer recurrence develops. Ahmed et al., *Frontiers in Oncology,* 3:256 (2013).

The treatment of ascites in women with epithelial ovarian, fallopian tube, and peritoneal cancers with, e.g., bevacizumab and aflibercept has been previously studied (Ferriss et al., *Gynecologic Oncology* (Abstracts), 133:2-207 (2014); Gotlieb et al., *Lancet Oncol.,* 13:154-62 (2012); and Colombo et al, *Gynecologic Oncology,* 125:42-47 (2012)). However, anti-angiogenic agents that target vascular endothelial growth factor A (VEGF-A) signaling pathways (such as bevacizumab and aflibercept) have demonstrated transient responses in the clinic, principally due to drug resistance. Abdollahi et al., *Drug Resist. Update,* 13:16-28 (2010); Bergers et al., *Nature Rev. Cancer,* 8:592-603 (2008); and Ebos et al., *Clin. Cancer Res.,* 15:5020-5025 (2009). In addition, anti-angiogenic agents targeting VEGF-A are associated with attenuated efficacy and class-specific toxicities (e.g., perforation of GI tract, hypertension, and proteinuria). Two general modes of resistance to angiogenesis inhibition (adaptive resistance and intrinsic non-responsiveness) have been elucidated. Indeed, both adaptive resistance and intrinsic non-responsiveness may stem from the factors such as the recruitment of hematopoietic and inflammatory cells into the tumors, the heterogeneity of genetically unstable tumor cells, and the presence of redundant angiogenic factors. Bergers et al., *Nature Rev. Cancer,* 8:592-603 (2008).

The angiopoietin-Tie system is not only crucial for angiogenesis and vascular homeostasis, but also provides a link between the inflammatory and angiogenic pathways. In light of the differences between the angiopoietin-Tie system and anti-angiogenic agents that target VEGF-A (such as bevacizumab and aflibercept), the use of agents which act as Ang2 and/or Tie2 inhibitors can address the outstanding need for an effective treatment of ovarian cancer in a human patient with ascites. In some cases, agents which act as Ang2 and/or Tie2 inhibitors can address the outstanding need for an effective treatment of ovarian cancer in a human patient with ascites, without the drawbacks associated with VEGF-A-targeting agents (e.g., attenuated efficacy and class-specific toxicities).

SUMMARY OF THE INVENTION

The present invention is directed, in one embodiment, to a method of treating ovarian cancer in a human patient with ascites by administering a therapeutically effective amount of an Ang2 inhibitor and/or a Tie2 inhibitor in combination with a taxane. In some embodiments the taxane is paclitaxel, docetaxel, or a derivative thereof. The Ang2 inhibitor of the present invention can be an antibody, Fc-peptide fusion protein (such as a peptibody), Fc-Tie2 extracellular domain (ECD) fusion protein (a "Tie2 trap"), or a small molecule inhibitor of Tie2.

For example, the Ang2 inhibitor may be an antibody or peptibody. In one embodiment, the Ang2 inhibitor is a dual Ang2 and Ang1 inhibitor. In another embodiment, the Ang2 inhibitor is the peptibody is 2XCon4(C) (i.e., AMG 386). In particular embodiments, the taxane is paclitaxel, docetaxel, or a derivative thereof. In other embodiments, the taxane is paclitaxel. In a specific embodiments, the method comprises treating ovarian cancer in a human patient with ascites by administering a therapeutically effective amount of 2XCon4 (C) in combination with paclitaxel.

The Ang2 inhibitor may be administered to a patient at a dose of about 3 mg/kg to about 20 mg/kg. In some embodiments, the Ang2 inhibitor is administered weekly.

In embodiments wherein the taxane is paclitaxel, it may be administered to a patient at a dose of about 80 mg/m². In some embodiments, paclitaxel is administered once a week for three of every four weeks (i.e., 3 weeks on, 1 week off).

The patient may be, in some embodiments, refractory to platinum based chemotherapy. In such embodiments, the platinum based chemotherapy is cisplatin, carboplatin, or oxaliplatin.

The invention further provides a method for treating ovarian cancer in a human patient with ascites by administering paclitaxel and 2XCon4(C). In another aspect, the invention further provides a method for treating ovarian cancer in a human patient with ascites by administering (a) 80 mg/m² of paclitaxel; and (b) 15 mg/kg 2XCon4(C). In addition, the invention further provides a method for treating ovarian cancer in a human patient with ascites by administering (a) 80 mg/m² of paclitaxel, via i.v., QW (3 weeks on/1 week off); and (b) 15 mg/kg 2XCon4(C), via i.v., QW (every week).

DETAILED DESCRIPTION

The present invention relates to compositions and methods for inhibiting progression of ovarian epithelial carcinomas in a human patient with ascites by administering a therapeutically effective amount of an Ang2 or Tie2 inhibitor in combination with a taxane, such as paclitaxel, docetaxel, or derivatives thereof.

The section headings are used herein for organizational purposes only, and are not to be construed as in any way limiting the subject matter described. The disclosure of all patents, patent applications, and other documents cited herein are hereby expressly incorporated by reference in their entirety. Unless specific definitions are provided, the nomenclature utilized in connection with, and the laboratory procedures and techniques of analytical chemistry, synthetic organic chemistry, and medicinal and pharmaceutical chemistry described herein are those well-known and commonly used in the art. Standard techniques may be used for chemical syntheses, chemical analyses, pharmaceutical preparation, formulation, and delivery, and treatment of patients.

Definitions

The terms used throughout this specification are defined as follows, unless otherwise limited in specific instances.

The term "Ang2" refers to the polypeptide set forth in FIG. 6 of U.S. Pat. No. 6,166,185 ("Tie2 ligand-2") as well as related native (i.e., wild-type) polypeptides such as allelic variants or splice variants (isoforms).

The term "Ang2 inhibitor" refers to an Ang2-specific binding agent that binds to human Ang2 and inhibits its binding to the human Tie2 receptor. In some embodiments, the Ang2-specific binding agent binds to human Ang2, inhibits its binding to the human Tie2 receptor, and results in a statistically significant decrease in angiogenesis, as measured by at least one functional assay of angiogenesis. Examples of such functional assays of angiogenesis include but are not limited to, tumor endothelial cell proliferation or the corneal micropocket assays (see, Oliner et al. Cancer Cell 6:507-516, 2004). See also, U.S. Pat. Nos. 5,712,291 and 5,871,723 (all of which are incorporated by reference). As those of ordinary skill in the art are aware, a corneal micropocket assay can be used to quantify the inhibition of angiogenesis. In this assay, agents to be tested for angiogenic activity are absorbed into a nylon membrane, which is implanted into micropockets created in the corneal epithelium of anesthetized mice or rats. Vascularization is measured as the number and extent of vessel ingrowth from the vascularized corneal limbus into the normally avascular cornea. See, U.S. Pat. No. 6,248,327 which describes planar migration and corneal pocket assays (hereby incorporated by reference). In certain embodiments, the Ang2 inhibitor is an antibody, avimer (Nature Biotechnology 23, 1556-1561 (2005)), peptibody (Fc-peptide fusion protein), Fc-soluble Tie2 receptor fusion (i.e., a "Tie2 trap"), or small molecule Ang2 inhibitor.

The term "antibody" includes reference to isolated forms of both glycosylated and non-glycosylated immunoglobulins of any isotype or subclass, including any combination of: 1) human (e.g., CDR-grafted), humanized, and chimeric antibodies; and 2) monospecific or multi-specific antibodies, monoclonal, polyclonal, or single chain (scFv) antibodies, irrespective of whether such antibodies are produced, in whole or in part, via immunization, through recombinant technology, by way of in vitro synthetic means, or otherwise. Thus, the term "antibody" is inclusive of those that are prepared, expressed, created or isolated by recombinant means, such as (a) antibodies isolated from an animal (e.g., a mouse) that is transgenic for human immunoglobulin genes or a hybridoma prepared therefrom; (b) antibodies isolated from a host cell transfected to express the antibody (e.g., from a transfectoma); (c) antibodies isolated from a recombinant, combinatorial antibody library; and (d) antibodies prepared, expressed, created or isolated by any other means that involve splicing of immunoglobulin gene sequences to other DNA sequences. In some embodiments the antibodies of the present invention are monoclonal antibodies, such as humanized or fully-human monoclonal antibodies. Typically, antibodies of the present invention will be IgG1 or IgG2 subclass antibodies. The antibody may bind Ang2 or Tie2 with a Kd of less than about 10 nM, 5 nM, 1 nM, or 500 pM.

The terms "derivation" or "derivative(s)" generally refer to modification of an Ang2 or Tie2 inhibitor (e.g., 2XCon4 (C)), or of a taxane (e.g., paclitaxel or docetaxel), by covalently linking it, directly or indirectly, so as to modify characteristics such as half-life, bioavailability, immunogenicity, solubility, or hypersensitivity, while retaining its therapeutic benefit. Derivatives can be made by, e.g., glycosylation, pegylation, and lipidation, or by protein conjugation of an Ang2 inhibitor, Tie2 inhibitor, or a taxane and are within the scope of the present invention. Exemplary derivitizing agents include an Fc domain as well as a linear polymer (e.g., polyethylene glycol (PEG), polylysine, dextran, etc.); a branched-chain polymer (see, e.g., U.S. Pat. Nos. 4,289,872; 5,229,490; and WO 93/21259—all of which are incorporated by reference); a lipid or liposome; a cholesterol group (such as a steroid); a carbohydrate or an oligosaccharide.

The terms "effective amount" or "therapeutically effective amount" when used in relation to an Ang2 or Tie2 inhibitor (e.g., 2XCon4(C)) refer to an amount that, when used in a combination therapy with a taxane (e.g., paclitaxel, docetaxel, or derivatives thereof): (a) inhibits ovarian cancer progression in a population of ovarian cancer patients with ascites; and/or (b) increases the length of time for progression-free survival (PFS) of a patient with ovarian cancer and ascites.

The term "Fc" in the context of an antibody or peptibody of the present invention is typically a fully human Fc, and may be any of the immunoglobulins (e.g., IgG1 and IgG2). However, Fc molecules that are partially human or obtained from non-human species are also included herein.

The term "Fc-peptide fusion" refers to a peptide that is covalently bonded, directly or indirectly, to an Fc. Exemplary Fc-peptide fusion molecules include a peptibody such as those disclosed in WO 03/057134 (hereby incorporated by reference) as well as an Fc covalently bonded, directly or indirectly, to an Ang2 specific binding fragment of the Tie2 receptor.

The term "host cell" refers to a cell that can be used to express a nucleic acid. A host cell can be a prokaryote, for example, E. coli, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al., Cell 23: 175, 1981), L cells, C127 cells, 3T3 cells (ATCC CCL 163), Chinese hamster ovary (CHO) cells or their derivatives such as Veggie CHO and related cell lines which grow in serum-free media (see Rasmussen et al., Cytotechnology 28: 31, 1998) or CHO strain DX-B11, which is deficient in DHFR (see Urlaub et al., Proc. Natl. Acad. Sci. USA 77: 4216-4220, 1980).

The term "human antibody" refers to an antibody in which both the constant and framework regions consist of fully or substantially all human sequences.

The term "humanized antibody" refers to an antibody in which all or substantially all of the constant region is derived from or corresponds to human immunoglobulins, while all or part of one or more variable regions is derived from another species, for example a mouse.

The term "isolated" refers to a compound that is: (1) is substantially purified (e.g., at least 60%, 70%, 80%, or 90%) away from cellular components with which it is admixed in its expressed state such that it is the predominant species present; (2) is conjugated to a polypeptide or other moiety to which it is not linked in nature; (3) does not occur in nature as part of a larger polypeptide sequence; (4) is combined with other chemical or biological agents having different specificities in a well-defined composition; or (5) comprises a human engineered sequence not otherwise found in nature.

The terms "monoclonal antibody" and "monoclonal antibody composition" refer to an antibody or a preparation of antibody molecules, respectively, wherein the antibody is made by identical immune cells that are all clones of a unique parent cell. Monoclonal antibodies all bind to the same epitope of a single molecular composition (i.e., they exhibit monovalent affinity). A monoclonal antibody composition displays a single binding specificity and affinity for a particular epitope. In certain embodiments, monoclonal antibodies are produced by a single hybridoma or other cell line (e.g., a transfectoma), or by a transgenic mammal. The term "monoclonal" is not limited to any particular method for making an antibody.

The terms "naturally occurring" or "native" when used in connection with biological materials such as nucleic acid molecules, polypeptides, host cells, and the like, refer to those which are found in nature and not modified by a human being.

The term "objective response (OR)" refers to the sum of observed complete and partial responses.

The terms, "oligonucleotide," "nucleic acid" and "polynucleotide" are used interchangeably throughout and refer to a deoxyribonucleotide or ribonucleotide polymer, or chimeras thereof, and unless otherwise limited, encompass the complementary strand of the referenced sequence. That is, the terms "oligonucleotide," "nucleic acid" and "polynucleotide" include DNA molecules (e.g., cDNA or genomic DNA), RNA molecules (e.g., mRNA), and hybrids thereof. The nucleic acid molecule can be single-stranded or double-stranded. A nucleic acid sequence is "operably linked" to a regulatory sequence if the regulatory sequence affects the expression (e.g., the level, timing, or location of expression) of the nucleic sequence.

The term "overall survival (OS)" refers to the fraction of subjects in an arm of a clinical trial who are alive at a given point in time following treatment with an active agent for the disease (e.g., ovarian cancer).

The terms "peptide," "polypeptide" and "protein" are used interchangeably throughout and refer to a molecule comprising two or more amino acid residues joined to each other by peptide bonds. "Polypeptides", "peptides" and "proteins" may be modified by, e.g., glycosylation, lipid attachment, sulfation, gamma-carboxylation of glutamic acid residues, hydroxylation and ADP-ribosylation.

The term "peptibody" refers to a specific binding agent that is a molecule comprising an antibody Fc domain attached to at least one peptide. The production of peptibodies is generally described in PCT publication WO 00/24782 (incorporated herein by reference). Exemplary peptides may be generated by any of the methods set forth therein, such as carried in a peptide library (e.g., a phage display library), generated by chemical synthesis, derived by digestion of proteins, or generated using recombinant DNA techniques.

The terms "peptibody fragment" or "antibody fragment" refer to a fragment of a peptibody or antibody wherein the fragment comprises less than a complete intact antibody or peptibody but retains the ability to specifically bind to its target molecule (e.g., Ang2). Exemplary fragments include F(ab) or F(ab')2 fragments. Such a fragment may arise, for example, from a truncation at the amino terminus, a truncation at the carboxy-terminus, and/or an internal deletion of a residue(s) from the amino acid sequence. Fragments may result from alternative RNA splicing or from in vivo or in vitro protease activity. Such fragments may also be constructed by chemical peptide synthesis methods, or by modifying a polynucleotide encoding an antibody or peptibody.

The term "progression free survival" (PFS) refers to the duration of time from the start of treatment to the time of progression of disease (measured radiographically or clinically) or death, whichever occurs first.

The term "regulatory sequence" refers to a nucleic acid that affects the expression (e.g., the level, timing, or location of expression) of a second nucleic acid. Thus, a regulatory sequence and a second sequence are operably linked if a functional linkage between the regulatory sequence and the second sequence is such that the regulatory sequence initiates and mediates transcription of the DNA sequence corresponding to the second sequence. Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., *Nucleic Acids Res.* 23: 3605-3606, 1995.

The term "specific binding agent" refers to, e.g., an Ang2 inhibitor or Tie2 inhibitor. A specific binding agent may be a protein, peptide, nucleic acid, carbohydrate, lipid, or small molecular weight compound that specifically binds to a target molecule such as Ang2 or Tie2. In one embodiment, the specific binding agent is an antibody or binding fragment thereof (e.g., Fab, F(ab')2), a peptide or a peptibody, an Fc-Tie2 extracellular domain (ECD) fusion protein ("Tie2 trap"), or Ang2 binding fragments thereof. WO 00/24782 and WO 03/057134 (incorporated herein by reference) describe making binding agents that contain a randomly generated peptide which binds a desired target. A specific binding agent can be a proteinaceous polymeric molecule (a "large molecule") such as an antibody or Fc-peptide fusion, or a non-proteinaceous non-polymeric molecule typically having a molecular weight of less than about 1200 Daltons (a "small molecule").

The term "specifically binds" refers to the ability of, e.g., a specific binding agent of the present invention, under specific binding conditions, to bind a target molecule such that its affinity is at least 10 times as great as the average affinity of the same specific binding agent to a collection of random peptides or polypeptides. In some embodiments, the specific binding agent binds a target molecule such that its affinity is 50, 100, 250, 500, or 1000 times as great as the average affinity of the same specific binding agent to a collection of random peptides or polypeptides. A specific binding agent need not bind exclusively to a single target molecule but may specifically bind to a non-target molecule due to similarity in structural conformation between the target and non-target (e.g., paralogs or orthologs). Those of skill will recognize that specific binding to a molecule having the same function in a different species of animal (i.e., ortholog) or to a molecule having a substantially similar epitope as the target molecule (e.g., a paralog) is within the scope of the term "specific binding" which is determined relative to a statistically valid sampling of unique non-targets (e.g., random polypeptides). Thus, a specific binding agent of the invention may specifically bind to more than one distinct species of target molecule, such as specifically binding to both Ang2 and Ang1. Solid-phase ELISA immunoassays can be used to determine specific binding. Generally, specific binding proceeds with an association constant of at least about $1 \times 10^7$ $M^{-1}$, and often at least $1 \times 10^8$ $M^{-1}$, $1 \times 10^9 M^{-1}$, or, $1 \times 10^{10}$ $M^{-1}$.

The term "Tie2 inhibitor" refers to a Tie2 specific binding agent that binds to human Tie2 and inhibits its binding to Ang2 and/or inhibits Tie2 signal transduction. In some embodiments, the Tie2 specific binding agent binds to human Tie2 and inhibits its binding to Ang2 and/or inhibits Tie2 signal transduction such that there is a decrease in angiogenesis, as measured by at least one functional assay of angiogenesis such as tumor endothelial cell proliferation or the corneal micropocket assay (Oliner et al. Cancer Cell 6:507-516, 2004). See also, U.S. Pat. Nos. 5,712,291 and 5,871,723 (both incorporated herein by reference). In certain embodiments, the Tie2 inhibitor is an antibody, avimer (Nature Biotechnology 23, 1556-1561 (2005)), peptibody, or small molecule Ang2 inhibitor.

As used herein, the terms "treatment", "treating", "inhibiting" or "inhibition" of ovarian cancer refer to at least one of: (a) a decrease in the rate of tumor growth; a cessation of tumor growth; or a reduction in the size, mass, metabolic activity, or volume of the tumor, as measured by standard criteria such as, but not limited to, the Response Evaluation Criteria for Solid Tumors (RECIST); (b) an increase in survival fraction at a given point of time relative to treatment with a taxane (e.g., paclitaxel or docetaxel) alone; or (c) an increase in the progression-free survival (PFS) of a patient with ovarian cancer and ascites.

The term "vector" refers to a nucleic acid used in the introduction of a polynucleotide of the present invention into a host cell. Vectors are often replicons. Expression vectors permit transcription of a nucleic acid inserted therein when present in a suitable host cell or under suitable in vitro conditions.

Combination Therapy for Treatment of Ovarian Cancer in Patients with Ascites

The present invention is directed to a method of treating ovarian epithelial carcinomas in a human patient with ascites with a combination of a specific binding agent and a taxane so as to inhibit, halt, reverse progression of the tumor. In some embodiments, the method of the present invention results in an increase in progression-free survival or overall survival. In other embodiments, the method of the present invention results in an increase in progression-free survival or overall survival relative to treatment with a taxane (e.g., paclitaxel or docetaxel) alone or a specific binding agent alone. The method comprises administering to the patient a therapeutically effective amount of an Ang2 and/or Tie2 inhibitor in combination with a taxane. In some embodiments, the patient is refractory to platinum based chemotherapy for ovarian cancer. Exemplary platinum based chemotherapeutics include cisplatin, carboplatin, and oxaliplatin.

The Ang2 and Tie2 inhibitors of the present invention are specific binding agents that inhibit interaction between Ang2 and its receptor Tie2 and/or inhibit Tie2 signal transduction thereby inhibiting tumor angiogenesis. In some embodiments, the Ang2 inhibitor also specifically binds to Ang1 and inhibits Ang1 binding to the Tie2 receptor (a "dual Ang2 and Ang1 inhibitor"). The Ang2 and Tie2 inhibitors are inclusive of large molecules such as a peptide, peptibody, antibody, antibody binding fragment such as a F(ab) or F(ab')2 fragment, an Fc-Tie2 extracellular domain (ECD) fusion protein (a "Tie2 trap"), and small molecules, or combinations thereof. In specific embodiments, the specific binding agent is an Ang2 inhibitory peptibody as discussed in more detail infra.

In the method of the present invention, a therapeutically effective amount of the specific binding agent (e.g., an Ang2 or Tie2 inhibitor) is administered in combination with a therapeutically effective amount of a taxane (as a chemotherapeutic agent). The therapeutically effective dose of the specific binding agent can be estimated initially either in cell culture assays or in animal models such as mice, rats, rabbits, dogs, pigs, or monkeys. An animal model may also be used to determine the appropriate concentration range and route of administration. Such information can then be used to determine useful doses and routes for administration in humans. The exact dosage will be determined in light of factors related to the subject requiring treatment. Dosage and administration are adjusted to provide sufficient levels of the active compound or to maintain the desired effect. Factors that may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

The frequency of dosing will depend upon the pharmacokinetic parameters of the specific binding agent molecule in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

The specific binding agent is administered at doses and rates readily determined by those of ordinary skill in the art. In some embodiments, the specific binding agent is an antibody or peptibody administered intravenously once a week. In some embodiments, the specific binding agent is an Ang2 or Tie2 inhibitor. In some embodiments, the specific binding agent is an Ang2 or Tie2 inhibitor (e.g., 2XCon4(C)) administered to the patient at a dose ranging from about 0.3 to about 30 mg/kg, about 1 to about 25 mg/kg, about 1 to about 20 mg/kg, or about 3 to about 15 mg/kg of patient body weight. In another embodiment, the specific binding agent is an Ang2 or Tie2 inhibitor (e.g., 2XCon4(C)) administered to the patient at a dose ranging from 0.3 to 30 mg/kg, 1 to 25 mg/kg, 1 to 20 mg/kg, or 3 to 15 mg/kg of patient body weight. For example, the Ang2 or Tie2 inhibitor (e.g., 2XCon4(C)) may be administered at a dose of 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, or 25 mg/kg. In another example, the Ang2 or Tie2 inhibitor (e.g., 2XCon4(C)) may be administered at a dose of about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, about 21 mg/kg, about 22 mg/kg, about 23 mg/kg, about 24 mg/kg, or about 25 mg/kg. In one embodiment, the Ang2 or Tie2 inhibitor (e.g., 2XCon4(C)) is administered at a dose of about 15 mg/kg. In another embodiment, the Ang2 or Tie2 inhibitor (e.g., 2XCon4(C)) is administered at a dose of 15 mg/kg. In a particular embodiment, 2XCon4(C) is administered at a dose of about 15 mg/kg. In another particular embodiment, 2XCon4(C) is administered at a dose of 15 mg/kg.

The taxane is administered at doses and rates readily determined by those of ordinary skill in the art. In some embodiments, the taxane is administered once a week (e.g., intravenously) for three weeks and is not administered the fourth week of a four week cycle (i.e., 3 weeks on/1 week off). In certain embodiments the taxane (e.g., paclitaxel) is administered once a week at approximately 40 to 120 mg/m$^2$ (square meter of patient surface area), 60 to 100 mg/m$^2$, or 70 to 90 mg/m$^2$. In other embodiments the taxane (e.g., paclitaxel) is administered once a week at about 40 to about 120 mg/m$^2$, about 60 to about 100 mg/m$^2$, or about 70 to about 90 mg/m$^2$. For example, the taxane (e.g., paclitaxel) may be administered at a dose of 65 mg/m$^2$, 66 mg/m$^2$, 67 mg/m$^2$, 68 mg/m$^2$, 69 mg/m$^2$, 70 mg/m$^2$, 71 mg/m$^2$, 72 mg/m$^2$, 73 mg/m$^2$, 74 mg/m$^2$, 75 mg/m$^2$, 76 mg/m$^2$, 77 mg/m$^2$, 78 mg/m$^2$, 79 mg/m$^2$, 80 mg/m$^2$, 81 mg/m$^2$, 82 mg/m$^2$, 83 mg/m$^2$, 84 mg/m$^2$, 85 mg/m$^2$, 86 mg/m$^2$, 87 mg/m$^2$, 88 mg/m$^2$, 89 mg/m$^2$, 90 mg/m$^2$, 91 mg/m$^2$, 92 mg/m$^2$, 93 mg/m$^2$, 94 mg/m$^2$, or 95 mg/m$^2$. In one embodiment, the taxane (e.g., paclitaxel) is administered at a dose of about 80 mg/m$^2$. In another example, the taxane (e.g., paclitaxel) is administered at a dose of about 65 mg/m$^2$, about 66 mg/m$^2$, about 67 mg/m$^2$, about 68 mg/m$^2$, about 69 mg/m$^2$, about 70 mg/m$^2$, about 71 mg/m$^2$, about 72 mg/m$^2$, about 73 mg/m$^2$, about 74 mg/m$^2$, about 75 mg/m$^2$, about 76 mg/m$^2$, about 77 mg/m$^2$, about 78 mg/m$^2$, about 79 mg/m$^2$, about 80 mg/m$^2$, about 81 mg/m$^2$, about 82 mg/m$^2$, about 83 mg/m$^2$, about 84 mg/m$^2$, about 85 mg/m$^2$, about 86 mg/m$^2$, about 87 mg/m$^2$, about 88 mg/m$^2$, about 89 mg/m$^2$, about 90 mg/m$^2$, about 91 mg/m$^2$, about 92 mg/m$^2$, about 93 mg/m$^2$, about 94 mg/m$^2$, or about 95 mg/m$^2$. In one embodiment, the taxane (e.g., paclitaxel) is administered at a dose of about 80 mg/m$^2$. In another embodiment, the taxane (e.g., paclitaxel) is administered at a dose of 80 mg/m$^2$. In a particular embodiment, paclitaxel is administered at a dose of about 80 mg/m$^2$. In another particular embodiment, paclitaxel is administered at a dose of 80 mg/m$^2$.

The administration of, e.g., 80 mg/m$^2$ of paclitaxel at a dosing regimen of 3 weeks on/1 week off has benefits compared to other dosing regimens of, e.g., 175 mg/m$^2$ of paclitaxel every 3 weeks. For example, administration of 80 mg/m$^2$ of paclitaxel at a dosing regimen of 3 weeks on/1 week off allows for more frequent dosing of lower amounts of paclitaxel (compared to 175 mg/m$^2$ of paclitaxel every 3 weeks). The 1 week off period also allows for patient recovery including, for example, allowing the patient to recover from paclitaxel-related bone marrow suppression.

The taxane of the present invention can be administered prior to and/or subsequent to (collectively, "sequential treatment"), and/or simultaneously with ("concurrent treatment") a specific binding agent of the present invention. Sequential treatment (such as pretreatment, post-treatment, or overlapping treatment) of the combination, also includes regimens in which the drugs are alternated, or wherein one component is administered long-term and the other(s) are administered intermittently. Components of the combination may be administered in the same or in separate compositions, and by the same or different routes of administration. Methods and dosing of administering chemotherapeutic agents are known in the art. Standard dosages and methods of administrations can be used, for example per the Food and Drug Administration (FDA) label. The taxane of the present invention may be given as a drip (infusion) through a cannula inserted into a vein (i.v.), through a central line, which is inserted under the skin into a vein near the collarbone, or a peripherally inserted central catheter (PICC) line. The dose of taxane is often administered in a fixed-time such as 30 minutes. Alternatively, the dose can be administered at a fixed rate (e.g., 10 mg/m$^2$/minute).

In a particular embodiment, the present invention relates to a method of treating ovarian cancer in a human patient with ascites comprising administering (a) 80 mg/m$^2$ of paclitaxel, via i.v., QW (3 weeks on/1 week off); and (b) 15 mg/kg 2XCon4(C), via i.v., QW (every week).

As demonstrated in Example 1, administration of 2XCon4 in combination with paclitaxel significantly improves OS among ovarian cancer patients with ascites. It is noted that the administration of 2XCon4 in combination with paclitaxel significantly improved OS among patients with recurrent and platinum sensitive or resistant ovarian cancer, with ascites.

Specific Binding Agents

Specific binding agents of the present invention are known in the art or may be prepared using methods known in the art. Exemplary Ang2 specific binding agents are disclosed in U.S. Pat. No. 7,138,370 (Oliner et al.); PCT WO 2006/068953 (Green et al.); U.S. Ser. No. 12/378,993 filed on Feb. 19, 2009 (Oliner et al.); PCT WO 2006/045049 (Oliner et al.), all of which are incorporated herein by reference. Exemplary Ang2 and Tie2 large molecule and small molecule inhibitors included within the scope of the present invention include: PF-4856884 (CovX 60; Pfizer), AP-25434 (Ariad), ARRY-614 (Array), CE-245677 (Pfizer), CEP-11981(Cephalon), SSR-106462 (Sanofi), MGCD-265 (Methylgene), CGI-1842 (CGI Pharma, Genentech), CGEN-25017 (Compugen), DX-2240 (Dyax, Sanofi), MEDI3617 (MedImmune), Antibody 3.19.3 (Astra Zeneca), and LP-590 (Locus Pharmaceuticals).

In a specific embodiment, the specific binding agent is 2XCon4(C) (alternatively referred to as AMG 386), a dual Ang2 and Ang1 inhibitor, as disclosed in U.S. Pat. No. 7,138,370 at SEQ ID NO: 25 (herein as SEQ ID NO: 1), wherein the Fc of SEQ ID NO: 25 is an IgG1 Fc such as that disclosed in SEQ ID NO: 60 (herein as SEQ ID NO: 2). In another embodiment the specific binding agent is antibody H4L4 disclosed in U.S. Ser. No. 12/378,993 (incorporated herein by reference) wherein the heavy chain has the sequence of SEQ ID NO: 3 of U.S. Ser. No. 12/378,993 (herein as SEQ ID NO: 3), and wherein the light chain has the sequence of SEQ ID NO: 10 of U.S. Ser. No. 12/378,993 (herein as SEQ ID NO: 4).

In general, specific binding agents such as antibodies, antibody fragments, peptibodies, avimers, or Fc-peptide fusions, that specifically bind and inhibit Tie2, Ang2, or Ang1 and Ang2 polypeptides are within the scope of the present invention. The antibodies may be isolated polyclonal or monoclonal (mAbs). The polyclonal or monoclonal antibodies can be chimeric, humanized such as CDR-grafted, fully human, single chain, bispecific, as well as antigen-binding fragments and/or derivatives thereof.

Monoclonal antibodies specifically binding to and functioning as an Ang2, a dual Ang2 and Ang1, or a Tie2 inhibitor can be produced using, for example but without limitation, the traditional "hybridoma" method or the newer "phage display" technique. For example, monoclonal antibodies of the invention may be made by the hybridoma method as described in Kohler et al., Nature 256:495 (1975); the human B-cell hybridoma technique (Kosbor et al., Immunol Today 4:72 (1983); Cote et al., Proc Natl Acad Sci (USA) 80: 2026-2030 (1983); Brodeur et al., Monoclonal Antibody Production Techniques and Applications, pp. 51-63, Marcel Dekker, Inc., New York, (1987)) and the EBV-hybridoma technique (Cole et al., Monoclonal Antibodies and Cancer Therapy, Alan R Liss Inc, New York N.Y., pp 77-96, (1985)).

The phage display technique may also be used to generate monoclonal antibodies. This technique is used to produce fully human monoclonal antibodies in which a polynucleotide encoding a single Fab or Fv antibody fragment is expressed on the surface of a phage particle. (Hoogenboom et al., J Mol Biol 227: 381 (1991); Marks et al., J Mol Biol 222: 581 (1991); see also U.S. Pat. No. 5,885,793, incorporated herein by reference)). Each phage can be "screened" using standard binding and cell-based assays to identify those antibody fragments having affinity for, and inhibition of, Ang2 or Tie2. Once polynucleotide sequences are identified which encode each chain of the full length monoclonal antibody or the Fab or Fv fragment(s) of the invention, host cells, either eukaryotic or prokaryotic, may be used to express the monoclonal antibody polynucleotides using recombinant techniques well known and routinely practiced in the art.

In another embodiment of the present invention, a monoclonal or polyclonal antibody or fragment thereof that is derived from other than a human species may be "humanized" or "chimerized". Methods for humanizing non-human antibodies are well known in the art. (see U.S. Pat. Nos. 5,859,205, 5,585,089, and 5,693,762—all of which are incorporated by reference). Humanization is performed, for example, using methods described in the art (Jones et al., Nature 321: 522-525 (1986); Riechmann et al., Nature, 332: 323-327 (1988); Verhoeyen et al., Science 239:1534-1536 (1988)) by substituting at least a portion of, for example a rodent, complementarity-determining region (CDRs) for the corresponding regions of a human antibody.

Alternatively, transgenic animals (e.g., mice) that are capable of producing a repertoire of human antibodies in the absence of endogenous immunoglobulin production can be used to generate such antibodies. This can be accomplished by immunization of the animal with an Ang2 or Tie2 antigen or fragments thereof (e.g., the Tie2 extracellular domain). Such immunogens can be optionally conjugated to a carrier. See, for example, Jakobovits et al., Proc Natl Acad Sci (USA), 90: 2551-2555 (1993); Jakobovits et al., Nature 362: 255-258 (1993); Bruggermann et al., Year in Immuno, 7: 33 (1993). In one method, such transgenic animals are produced by incapacitating the endogenous loci encoding the heavy and light immunoglobulin chains therein, and inserting loci encoding human heavy and light chain proteins into the genome thereof. Partially modified animals, that are those having less than the full complement of these modifications, are then crossbred to obtain an animal having all of the desired immune system modifications. When administered an immunogen, these transgenic animals are capable of producing antibodies with human variable regions, including human (rather than e.g., murine) amino acid sequences, that are immuno-specific for the desired antigens.

See PCT application Nos., PCT/US96/05928 and PCT/US93/06926 (all of which are incorporated by reference). Additional methods are described in U.S. Pat. No. 5,545,807, PCT application Nos. PCT/US91/245, PCT/GB89/01207, and in EP 546073B1 and EP 546073A1 (all of which are incorporated by reference). Human antibodies may also be produced by the expression of recombinant DNA in host cells or by expression in hybridoma cells as described herein.

Large-scale production of chimeric, humanized, CDR-grafted, and fully human antibodies, or antigen-binding fragments thereof, are typically produced by recombinant methods. Polynucleotide molecule(s) encoding the heavy and light chains of each antibody or antigen-binding fragments thereof, can be introduced into host cells and expressed using materials and procedures described herein. In a particular embodiment, the antibodies are produced in mammalian host cells, such as CHO cells.

Taxanes

In some embodiments the taxane of the present invention is paclitaxel (TAXOL), docetaxel (TAXOTERE), or taxane derivatives such as ABRAXANE (albumin-bound paclitaxel), Poly-(L-glutamic acid)-paclitaxel (PG-paclitaxel), TAXOPREXIN (DHA-paclitaxel), or pegylated liposomal doxorubicin. In one embodiment, the taxane of the present invention is paclitaxel.

Pharmaceutical Compositions

The pharmaceutical composition may contain formulation materials for modifying, maintaining or preserving, for example, the pH, osmolarity, viscosity, clarity, color, isotonicity, odor, sterility, stability, rate of dissolution or release, adsorption, or penetration of the composition. Such pharmaceutical compositions may comprise the Ang2 and/or Tie2 inhibitor of the present invention, the taxane of the present invention, or both. For example, a pharmaceutical composition of the present invention may comprise 2XCon4 (C), paclitaxel, or both.

The primary vehicle or carrier in a pharmaceutical composition may be either aqueous or non-aqueous in nature. For example, a suitable vehicle or carrier may be water for injection or physiological saline, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute therefore. In one embodiment of the present invention, pharmaceutical compositions may be prepared for storage by mixing the selected composition having the desired degree of purity with optional formulation agents (Remington's Pharmaceutical Sciences, supra) in the form of a lyophilized cake or an aqueous solution. Further, the pharmaceutical composition may be formulated as a lyophilizate using appropriate excipients such as sucrose.

The formulation components are present in concentrations that are acceptable to the site of administration. For example, buffers are used to maintain the composition at physiological pH or at slightly lower pH, typically within a pH range of from about 5 to about 8. A particularly suitable vehicle for parenteral administration is sterile distilled water in which a binding agent is formulated as a sterile, isotonic solution, properly preserved. Yet another preparation can involve the formulation of the desired molecule with an agent, such as injectable microspheres, bio-erodible particles, polymeric compounds (polylactic acid, polyglycolic acid), beads, or liposomes, that provide for the controlled or sustained release of the product which may then be delivered via a depot injection.

In another aspect, pharmaceutical formulations suitable for parenteral administration may be formulated in aqueous solutions (e.g., in physiologically compatible buffers such as Hanks' solution, ringer's solution, or physiologically buffered saline). Aqueous injection suspensions may contain substances that increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

The pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration. In a specific embodiment, a lyophilized peptibody, such as 2XCon4(C), is formulated as disclosed in WO 2007/124090 (incorporated herein by reference).

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes). Kits of the present invention may contain instructions for administering the Ang2 and/or Tie2 inhibitor of the present invention (e.g., 2XCon4(C)), the taxane of the present invention (e.g., paclitaxel), or both. In one embodiment, the kit instructions provide directions for administering, to a human patient with ovarian cancer and ascites: (a) 80 mg/m2 of paclitaxel, via i.v., QW (3 weeks on/1 week off); and (b) 15 mg/kg 2XCon4(C), via i.v., QW (every week).

An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the binding agent molecule is being used, the route of administration, and the size (body weight, body surface or organ size) and condition (the age and general health) of the patient. Accordingly, the clinician may titer the dosage and modify the route of administration to obtain the optimal therapeutic effect.

Typical dosages for pharmaceutical compositions comprising a specific binding agent (e.g., an Ang2 or Tie2 inhibitor such as 2XCon4(C)) range from 0.3 to 30 mg/kg, 1 to 25 mg/kg, 1 to 20 mg/kg, or 3 to 15 mg/kg of patient body weight. For example, dosages for pharmaceutical compositions comprising a specific binding agent (e.g., an Ang2 or Tie2 inhibitor such as 2XCon4(C)) may be 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, or 25 mg/kg.

Typical dosages for pharmaceutical compositions comprising a taxane (e.g., paclitaxel) range from 40 to 120 mg/m$^2$, 60 to 100 mg/m$^2$, or 70 to 90 mg/m$^2$. For example, dosages for pharmaceutical compositions comprising a taxane may be 65 mg/m$^2$, 66 mg/m$^2$, 67 mg/m$^2$, 68 mg/m$^2$, 69 mg/m$^2$, 70 mg/m$^2$, 71 mg/m$^2$, 72 mg/m$^2$, 73 mg/m$^2$, 74 mg/m$^2$, 75 mg/m$^2$, 76 mg/m$^2$, 77 mg/m$^2$, 78 mg/m$^2$, 79 mg/m$^2$, 80 mg/m$^2$, 81 mg/m$^2$, 82 mg/m$^2$, 83 mg/m$^2$, 84 mg/m$^2$, 85 mg/m$^2$, 86 mg/m$^2$, 87 mg/m$^2$, 88 mg/m$^2$, 89 mg/m$^2$, 90 mg/m$^2$, 91 mg/m$^2$, 92 mg/m$^2$, 93 mg/m$^2$, 94 mg/m$^2$, or 95 mg/m$^2$.

In a particular embodiment, the present invention relates to pharmaceutical compositions comprising (a) paclitaxel; (b) 2XCon4(C), or both. In another embodiment, the present invention relates to pharmaceutical compositions comprising (a) paclitaxel in an amount suitable for administering to a patient 80 mg/m$^2$, via i.v., QW (3 weeks on/1 week off); (b) 2XCon4(C) in an amount suitable for administering to a patient 15 mg/kg, via i.v., QW (every week), or both.

The above listings are by way of example only, and do not preclude the use of other compounds or treatments which can be used concurrently with the compounds described herein that are known by those skilled in the art or that could be arrived at by those skilled in the art using the guidelines set forth in this specification.

Example 1

Example 1 is a description of a Phase 3, randomized, double-blind trial of weekly paclitaxel plus AMG 386 (2XCon4(C)) or placebo in women with recurrent partially platinum sensitive or resistant epithelial ovarian, primary peritoneal or fallopian tube cancers. Details of this study can be found at the US National Institutes of Health website (clinicaltrials.gov), under study identifier: NCT01204749 (incorporated herein by reference).

The primary objective of the study was to determine whether treatment with paclitaxel plus AMG 386 is superior to paclitaxel plus placebo in women with recurrent partially platinum sensitive or resistant epithelial ovarian cancer, primary peritoneal cancer or fallopian tube cancer.

919 women with recurrent epithelial ovarian cancer (platinum-free interval<12 mo) were randomized to paclitaxel 80 mg/m$^2$ IV QW (3 wks on/1 wk off) plus either [i] blinded trebananib 15 mg/kg IV QW (trebananib+paclitaxel); or [ii] placebo (paclitaxel alone). Treatment continued until progression, toxicity or consent withdrawal.

The primary outcome measure was progression free survival (PFS).

Secondary Outcome Measures were:
Overall survival (Time Frame: 20 months on average)
Objective Response Rate (Time Frame: From Baseline, if subject has Measurable Disease, until objective response (radiologic)
Duration of response (Time Frame: From Baseline until progression)

CA-125 response rate per Gynecologic Cancer Intergroup (GCIG) and change in CA-125 (Time Frame: From Baseline until CA-125 response)
Incidence of adverse events and significant laboratory abnormalities (Time Frame: 8 Months on average)
Pharmacokinetics of AMG 386 (Cmax and Cmin) (Time Frame: Week 1 until week 9 of treatment)
Incidence of the occurrence of anti-AMG 386 antibody formation (Time Frame: Week 1 until maximum of 1-year following last dose of study drug)
Patient reported Health Related Quality of Life (HRQOL) and ovarian cancer related symptoms using Functional Assessment of Cancer Therapy-Ovary questionnaire (FACT-O) (Time Frame: From week 1 until 30-days following last study drug administration)
Overall health status using EuroQOL (EQ-5D) (Time Frame: From week 1 until 30-days following last study drug administration Inclusion Criteria:
Female 18 years of age or older at the time the written informed consent is obtained
Gynecologic Oncology Group (GOG) Performance Status of 0 or 1
Life expectancy≥3 months (per investigator opinion)
Histologically or cytologically documented invasive epithelial ovarian cancer, primary peritoneal cancer, or fallopian tube cancer
  Subjects with pseudomyxoma, mesothelioma, unknown primary tumor, sarcoma, or neuroendocrine histology, with borderline ovarian cancer (i.e., subjects with low malignant potential tumors), and with clear cell or mucinous histology are excluded
Subjects must have undergone surgery for ovarian cancer, primary peritoneal cancer, or fallopian tube cancer including at least a unilateral oophorectomy
Radiologically evaluable disease per Response Evaluation Criteria in Solid Tumors (RECIST) 1.1 with modifications
Subjects must have had one prior platinum-based chemotherapeutic regimen for management of primary disease containing carboplatin, cisplatin, or another organoplatinum compound.
  This initial treatment may have included intraperitoneal therapy, high-dose therapy, consolidation therapy, bevacizumab or extended therapy administered after surgical or non-surgical assessment.
Adequate organ and hematological function
Generally well controlled blood pressure with systolic blood pressure≤140 mmHg and diastolic blood pressure≤90 mmHg prior to randomization. The use of anti-hypertensive medications to control hypertension is permitted
Radiographically documented disease progression either on or following the last dose of prior chemotherapy regimen for epithelial ovarian cancer, primary peritoneal cancer, or fallopian tube cancer Exclusion Criteria
Subjects who have received more than 3 previous regimens of anti-cancer therapy for epithelial ovarian, primary peritoneal or fallopian tube cancers
Subjects who have received paclitaxel as consolidation therapy, maintenance, or monotherapy are excluded
Subjects with primary platinum-refractory disease having progressed on platinum therapy
Subjects with platinum-free interval (PFI)>12 months from their last platinum based therapy
Radiotherapy≤14 days prior to randomization Subjects must have recovered from all radiotherapy-related toxicities
Previous abdominal or pelvic radiotherapy
History of arterial or venous thromboembolism within 12 months prior to randomization
History of clinically significant bleeding within 6 months prior to randomization
History of central nervous system metastasis
Has not yet completed a 21 day washout period prior to randomization for any previous anti-cancer systemic therapies (30 days for prior bevacizumab)
Enrolled in or has not yet completed at least 30 days (prior to randomization) since ending other investigational device or drug, or currently receiving other investigational treatments
Unresolved toxicities from prior systemic therapy that are Common Terminology Criteria for Adverse Events (CTCAE) Version 3.0≥Grade 2 in severity except alopecia
Known active or ongoing infection (except uncomplicated urinary tract infection) within 14 days prior to randomization
Currently or previously treated with AMG 386, or other molecules that inhibit the angiopoietins or Tie2 receptor
Treatment within 30 days prior to randomization with strong immune modulators including but not limited to systemic cyclosporine, tacrolimus, sirolimus, mycophenolate mofetil, methotrexate, azathioprine, rapamycin, thalidomide, and lenalidomide
Clinically significant cardiovascular disease within 12 months prior to randomization
Major surgery within 28 days prior to randomization or still recovering from prior surgery
Minor surgical procedures, except placement of tunneled central venous access device within 3 days prior to randomization
Diagnostic laparoscopy is regarded as a minor surgical procedure Subjects were Randomized in a 1:1 Ratio to Each of the Following Arms:

Arm A: Paclitaxel 80 mg/m$^2$ IV QW (3 weeks on/1 week off) plus blinded AMG 386 15 mg/kg IV QW Arm B: Paclitaxel 80 mg/m$^2$ IV QW (3 weeks on/1 week off) plus blinded AMG 386 placebo IV QW Subjects received paclitaxel plus AMG 386 or placebo (depending on treatment arm) until disease progression per RECIST 1.1 with modifications, until the subject experienced unacceptable toxicity, withdrew consent or died. Subjects who discontinued paclitaxel for reasons other than disease progression per RECIST 1.1 with modifications, withdrawal of consent, or death continued to receive AMG 386 or placebo. Subjects who discontinued AMG 386 or placebo for reasons other than disease progression per RECIST 1.1 with modifications, withdrawal of consent, or death continued to receive paclitaxel.

Results

After median follow-up of 17.7 months and 628 OS events, median OS (ITT) was 19.3 months with trebananib+paclitaxel vs 18.3 months with paclitaxel alone (HR=0.95, 95% CI, 0.81-1.12; p=0.55).

The pre-specified subgroup analysis of OS also evaluated 295 (32%) patients with ascites. Baseline characteristics did not differ between patients with and without ascites, and patients with ascites randomized to trebananib+paclitaxel vs paclitaxel alone. Trebananib+paclitaxel improved OS among patients with ascites by 2.2 months (median 14.5 vs 12.3 months with paclitaxel alone; HR=0.72, 95% CI 0.55-0.93; p=0.011). After on-study progression, 684 (74%) patients received a median of 2 (range, 1-8) additional lines of therapy. PFS2 in the trebananib+paclitaxel arm increased by 1.6 months (median 12.5 vs 10.9 months with paclitaxel alone; HR=0.85, 95% CI 0.74-0.98; p=0.025). Analysis of time to second subsequent therapy (TSST) confirmed the PFS2 result (13.4 vs 11.7 months with paclitaxel alone; HR=0.83, 95% CI, 0.72-0.96; p=0.011). The incidence of grade≥3 adverse events (AEs) was 60% for trebananib+paclitaxel vs 56% for paclitaxel alone. Trebananib+paclitaxel was associated with more AE-related treatment discontinuations (22% vs 8%) and localized edema events (any grade, 59% vs 27%).

Accordingly, administration of 2XCon4 in combination with paclitaxel significantly improved OS among patients with ascites. It is particularly relevant that the administration of 2XCon4 in combination with paclitaxel significantly improved OS among patients with recurrent and platinum sensitive or resistant ovarian cancer, with ascites.

What is claimed:

1. A method for treating ovarian cancer, comprising administering to a human ovarian cancer patient with ascites a therapeutically effective amount of an Ang2 inhibitor in combination with a taxane, wherein said patient has recurrent partially platinum sensitive ovarian cancer, or platinum-resistant ovarian cancer.

2. The method of claim 1, wherein said Ang2 inhibitor is an antibody or peptibody.

3. The method of claim 2, wherein said Ang2 inhibitor is a dual Ang2 and Ang1 inhibitor.

4. The method of claim 1, wherein said Ang2 inhibitor is trebananib.

5. The method of claim 1, wherein said taxane is paclitaxel, docetaxel, or a derivative thereof.

6. The method of claim 5, wherein said Ang2 inhibitor is administered to said patient at a dose of about 3 mg/kg to about 20 mg/kg.

7. The method of claim 6, wherein said Ang2 inhibitor is administered weekly.

8. The method of claim 7, wherein said taxane is paclitaxel administered to said patient at a dose of about 80 mg/m$^2$.

9. The method of claim 8, wherein said paclitaxel is administered once a week for three of every four weeks.

10. The method of claim 1, comprising administering to a human ovarian cancer patient with ascites: (a) 80 mg/m$^2$ of paclitaxel, via i.v., once a week for three weeks and not administering paclitaxel the fourth week of a four week cycle; and (b) 15 mg/kg trebananib, via i.v., once weekly.

11. A method for treating ovarian cancer, comprising administering to a human ovarian cancer patient with ascites an Ang2 inhibitor at a weekly dose of about 3 mg/kg to about 20 mg/kg in combination with paclitaxel at a dose of about 80 mg/m$^2$ once a week for three of every four weeks, wherein said patient is refractory to platinum based chemotherapy.

12. The method of claim 11 wherein said platinum based chemotherapy is cisplatin, carboplatin, or oxaliplatin.

13. The method of claim 11, wherein said Ang2 inhibitor is an antibody or peptibody.

14. The method of claim 11, wherein said Ang2 inhibitor is trebananib.

15. A method for treating ovarian cancer, comprising administering to a human ovarian cancer patient with ascites a therapeutically effective amount of an Ang2 inhibitor in combination with a taxane, wherein said Ang2 inhibitor is a monoclonal antibody.

16. The method of claim 15, wherein said taxane is paclitaxel, docetaxel, or a derivative thereof.

17. The method of claim 16, wherein said taxane is paclitaxel administered to said patient at a dose of about 80 mg/m$^2$.

18. The method of claim 17, wherein said paclitaxel is administered once a week for three of every four weeks.

* * * * *

SEQUENCE LISTING

```
<160> NUMBER OF SEQ ID NOS: 4

<210> SEQ ID NO 1
<211> LENGTH: 287
<212> TYPE: PRT
<213> ORGANISM: Artificial Sequence
<220> FEATURE:
<223> OTHER INFORMATION: Peptibody capsule of binding to Ang-2

<400> SEQUENCE: 1

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60
```

```
Val His Asn Ala Lys Thr Lys Pro Arg Glu Glu Gln Tyr Asn Ser Thr
 65                  70                  75                  80

Tyr Arg Val Val Ser Val Leu Thr Val Leu His Gln Asp Trp Leu Asn
                 85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys Gly Gly Gly Gly Ala Gln Gln Glu Glu Cys Glu
225                 230                 235                 240

Trp Asp Pro Trp Thr Cys Glu His Met Gly Ser Gly Ser Ala Thr Gly
                245                 250                 255

Gly Ser Gly Ser Thr Ala Ser Ser Gly Ser Gly Ser Ala Thr His Gln
            260                 265                 270

Glu Glu Cys Glu Trp Asp Pro Trp Thr Cys Glu His Met Leu Glu
        275                 280                 285

<210> SEQ ID NO 2
<211> LENGTH: 227
<212> TYPE: PRT
<213> ORGANISM: Artificial Sequence
<220> FEATURE:
<223> OTHER INFORMATION: Human Fc IgG1

<400> SEQUENCE: 2

Asp Lys Thr His Thr Cys Pro Pro Cys Pro Ala Pro Glu Leu Leu Gly
  1               5                  10                  15

Gly Pro Ser Val Phe Leu Phe Pro Pro Lys Pro Lys Asp Thr Leu Met
                 20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140
```

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 3
<211> LENGTH: 122
<212> TYPE: PRT
<213> ORGANISM: Homo sapiens

<400> SEQUENCE: 3

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Asp Tyr Asp Leu Leu Thr Gly Tyr Gly Tyr Trp
            100                 105                 110

Gly Gln Gly Thr Leu Val Thr Val Ser Ser
        115                 120

<210> SEQ ID NO 4
<211> LENGTH: 112
<212> TYPE: PRT
<213> ORGANISM: Homo sapiens

<400> SEQUENCE: 4

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

His Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Thr Phe Gly Gln Gly Thr Lys Leu Glu Ile Lys
            100                 105                 110